US00PP26823P2

(12) United States Plant Patent
Shoji

(10) Patent No.: US PP26,823 P2
(45) Date of Patent: Jun. 14, 2016

(54) *HYDRANGEA* PLANT NAMED 'B-003'

(50) Latin Name: *Hydrangea macrophylla*
Varietal Denomination: B-003

(71) Applicant: Sakamoto Shoji, Gumma-Ken (JP)

(72) Inventor: Sakamoto Shoji, Gumma-Ken (JP)

( * ) Notice: Subject to any disclaimer, the term of this patent is extended or adjusted under 35 U.S.C. 154(b) by 112 days.

(21) Appl. No.: 14/121,479

(22) Filed: Sep. 10, 2014

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla*, 'B-003', that is characterized by its free flowering plant habit, its uniform mophead type inflorescences comprised of double sterile flowers with small sepals that are dark pink in color, its lack of fertile flowers, and its leaves that are ovate in shape and dark green in color.

2 Drawing Sheets

Botanical classification: *Hydrangea macrophylla.*
Varietal denomination: 'B-003'.

BACKGROUND OF THE INVENTION

The present invention relates to a new and distinct cultivar of *Hydrangea macrophylla* and will be referred to hereafter by its cultivar name, 'B-003'. 'B-003' represents a new mophead type *Hydrangea*, a deciduous shrub grown for landscape use and for use as a potted plant.

The new cultivar is the result of a controlled breeding program conducted by the Inventor in Kurohonemura, Gunma Prefecture, Japan. The new cultivar arose from a cross made in 2008 between unnamed proprietary plants in the Inventor's breeding program; reference no. W-4 as the female parent and reference no. V-5 as the male parent. 'B-003' was selected as single unique plant amongst the seedling from the above cross in 2010.

Asexual reproduction of the new cultivar was first accomplished by the Inventor using softwood stem cuttings in 2010 in Gunma Prefecture, Japan. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'B-003' as a unique cultivar of *Hydrangea macrophylla.*

1. 'B-003' exhibits a free flowering plant habit.
2. 'B-003' exhibits uniform mophead type inflorescences comprised of double sterile flowers with small sepals that are dark pink in color.
3. 'B-003' lacks fertile flowers.
4. 'B-003' exhibits leaves that are ovate in shape and dark green in color.

'W-4', the female parent of 'B-003', differs from 'B-003' in having flower heads that are less uniformly mophead in form and in having leaves that are more oval in shape with darker colored margins. 'V-5', the male parent of 'B-003', differs from 'B-003' in having sterile flower sepals that are larger in size and leaves that are larger in size. 'B-003' can be most closely compared to the cultivars 'RIE 05' (U.S. Plant Pat. No. 18,508) and 'Perfection' (U.S. Plant Pat. No. 22,221). Both are similar to 'B-003' in having double sterile flowers and in being free flowering. 'RIE 05' differs from 'B-003' in having leaves that are lighter in color, in having a less vigorous growth rate, and in having sterile flowers that are lighter pink in color with larger sepals. 'Perfection' differs from 'RIE 05' in having sterile flowers with larger sepals that are lighter pink in color and elliptic in shape.

BRIEF DESCRIPTION OF THE DRAWINGS

The accompanying colored photographs illustrate the overall appearance and distinct characteristics of the new *Hydrangea*. The photographs were taken of cut stems from a two year-old plant as grown in a greenhouse in a 5-liter container in De Kwakel, The Netherlands.

The photograph in FIG. 1 provides a side view of the of 'B-003' in bloom.

Figure 1:
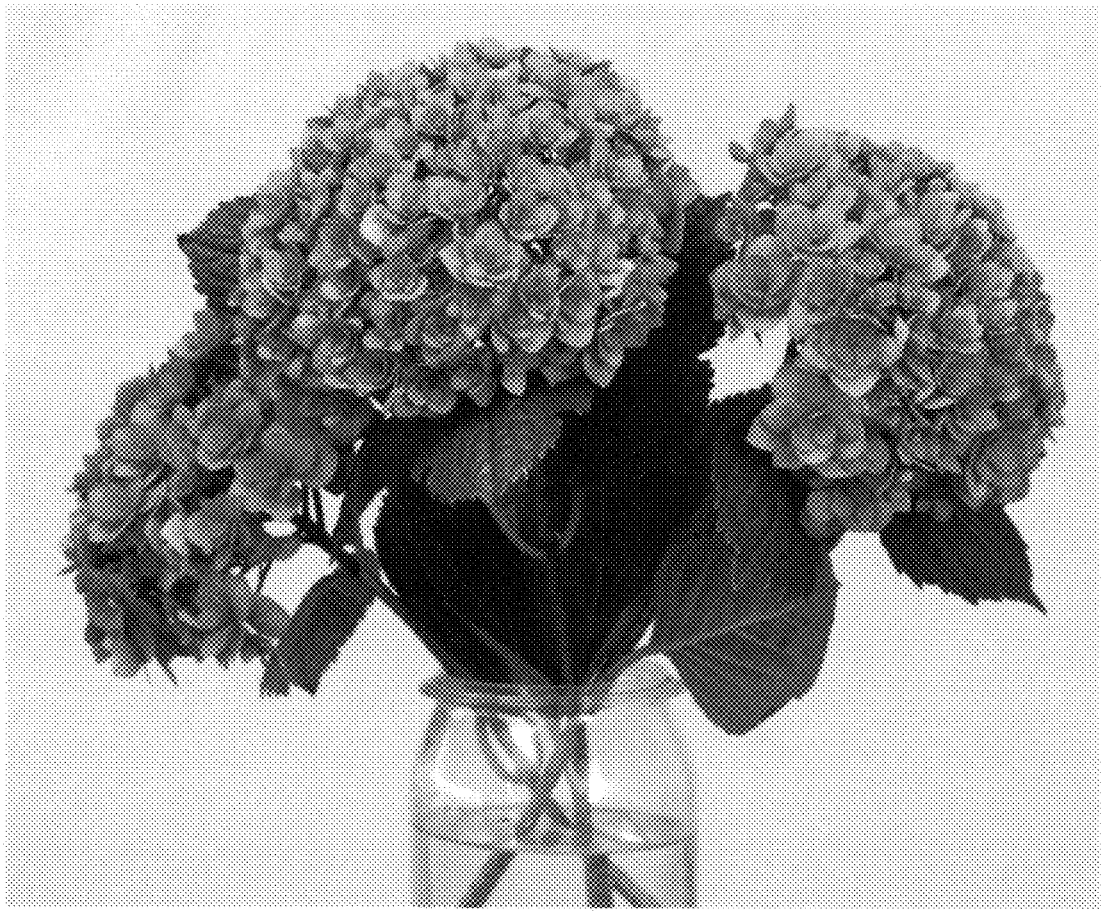
Figure 2:
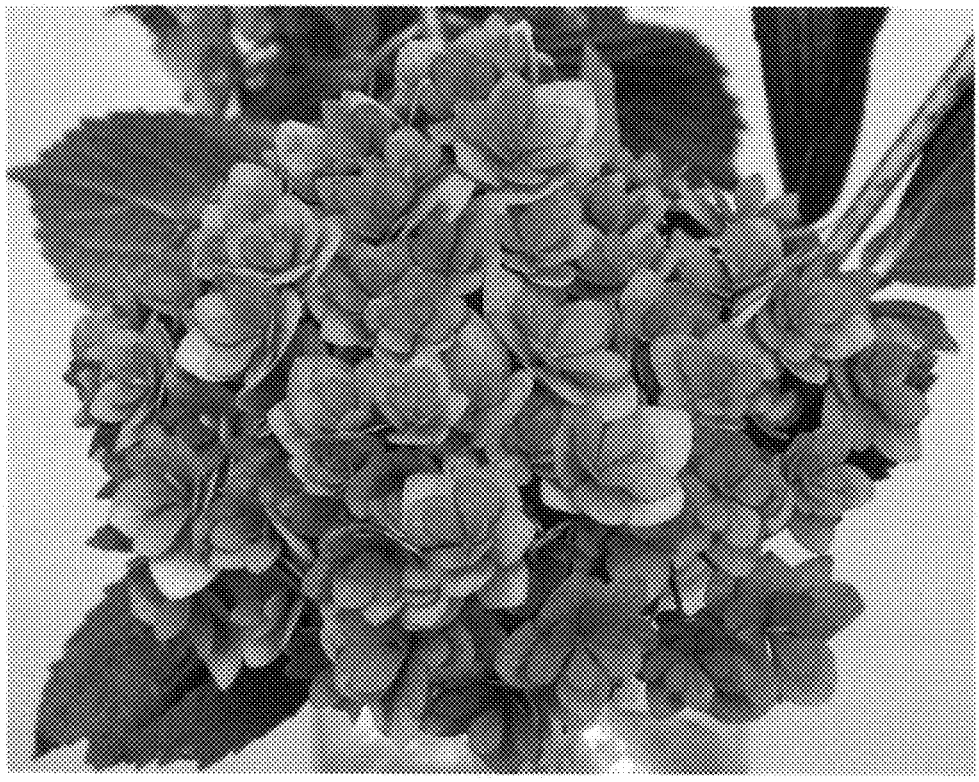

The photograph in FIG. 2 provides a close-up view of an inflorescence of 'B-003'.

Figure 3:
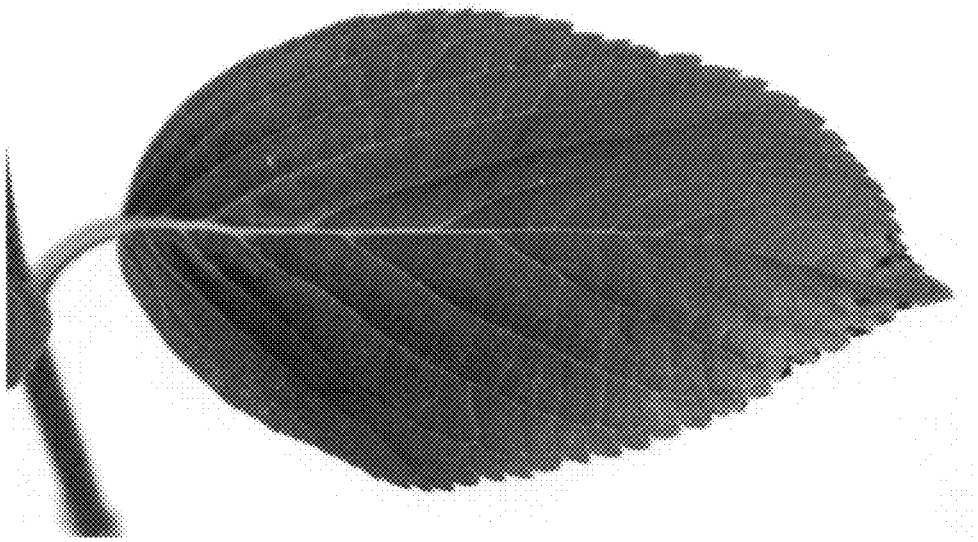

The photograph in FIG. 3 provides a close-up view of a leaf of 'B-003'.

The colors in the photographs are as close as possible with the digital photographic and printing techniques utilized and the color codes in the detailed botanical description accurately describe the new *Hydrangea.*

BOTANICAL DESCRIPTION OF THE PLANT

The following is a detailed description of two year-old plants of 'B-003' as grown in a greenhouse in 5-liter containers in De Kwakel, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—June to September.

*Plant type*.—Deciduous shrub, mophead type *Hydrangea*.

*Plant habit*.—Broad upright, broad inverted triangle shape.

*Height and spread*.—An average of 60 cm in height and 90 cm in width.

*Hardiness*.—At least in U.S.D.A. Zones 5 to 9.

*Pest and diseases*.—Has been observed to have some resistance to spider mites under the conditions grown and no disease resistance or susceptibility has been observed.

*Root description*.—Fine.

*Propagation*.—Softwood stem cuttings.

*Growth rate and vigor*.—Vigorous.

Stem description:

*Stem shape*.—Round, solid.

*Stem strength*.—Strong.

*Stem color*.—Young growth; a color between 143C and 144C and slightly tinged 187A to 187B at the nodes, mature growth; 199A to 199B.

*Stem size*.—Up to 42.5 cm (excluding inflorescence), average of 7 mm in diameter.

*Stem surface*.—Glabrous.

*Internode length*.—Average of 6.9 cm.

*Branching*.—An average of 12 basal branches, held at an average angle of 45° to soil level, moderately free branching.

*Lenticels*.—Densely covered, average of 15 per squared cm, average of 0.75 mm in length and width and N186C in color.

Foliage description:

*Leaf shape*.—Ovate.

*Leaf arrangement*.—Opposite.

*Leaf division*.—Simple.

*Leaf base*.—Attenuate.

*Leaf apex*.—Broad apiculate.

*Leaf margins*.—Serrate.

*Leaf venation*.—Pinnate, color upper surface; 145A to 145B, color lower surface; 145A.

*Leaf size*.—An average of 13.9 cm in length and 9.4 cm in width.

*Leaf attachment*.—Petiolate.

*Leaf surface*.—Upper surface glabrous, moderately glossy and very slightly rugose, lower surface smooth, slightly glossy and very slightly rugose.

*Leaf color*.—Young upper surface; N137B, young lower surface; between 143A and 146A, mature upper surface; between N137A, N137B and 141A, mature lower surface; 146A to 146B.

*Petioles*.—Average of 2.5 cm in length and 3.5 mm in diameter, both surfaces 145A in color, surface glabrous and moderately glossy.

Inflorescence description:

*Inflorescence type*.—Terminal compound corymb, mophead in form, comprised of sterile flowers, lacks fertile flowers, all descriptors are foe sterile flowers.

*Lastingness of inflorescence*.—Persistent but color is retained for about 3 weeks.

*Inflorescence number*.—One per lateral or sublateral stem if pinched.

*Inflorescence size*.—Average of 9.7 cm in height and 18.6 cm in diameter.

*Flower number*.—Average of 160 sterile flowers.

*Flower fragrance*.—None.

*Flower aspect*.—Held upright to outward to slightly drooping.

*Flower size*.—Average of 4.1 cm in diameter and 1.6 cm in depth.

*Flower type*.—Rotate.

*Flower buds*.—Average of 7 mm in length and 4 mm in width, ovate in shape, color; 150D, tinged N78D at apex.

*Pedicels*.—Held at an average angle of 20° to main peduncle, strong, matte and glabrous surface, color is N79D, average of 1.6 cm in length and 1 mm in diameter.

*Petals*.—None present.

*Sepals*.—Sterile flowers; average of 14, rotate, rhomboidal to ovate in shape, an average of 2.3 cm in length and 1.7 cm in width, bluntly acute apex, cuneate base, upper surface is glabrous, matte and moderately velvety, lower surface is glabrous and matte, entire margins, color: when opening upper surface; N74C, veined 86D, when opening lower surface; 75A, veined 86D, fully opened upper surface; 70A, fully opened lower surface; 70B, tinged 77B at the top, upper surface fading to N80C to N80D, lower surface fading to N80D.

Reproductive organs:

*Stamens*.—No androecium.

*Pistils*.—Present on some sterile flowers), average of 3, average of 1 mm in length, stigma is club-shaped and N155A in color, style is an average of 0.75 mm in length and 92B to 92C in color, ovary is 150D in color.

*Fruit and seed*.—No fruit or seed observed to date.

It is claimed:

1. A new and distinct cultivar of *Hydrangea* plant named 'B-003' substantially as herein illustrated and described.

* * * * *